US011614587B2

(12) United States Patent
Kulkarni (10) Patent No.: US 11,614,587 B2
(45) Date of Patent: Mar. 28, 2023

(54) FIBER OPTIC TAPERED COUPLER

(71) Applicant: Devashish R. Kulkarni, Berkeley, CA (US)

(72) Inventor: Devashish R. Kulkarni, Berkeley, CA (US)

(73) Assignee: MEDICAL INSTRUMENT DEVELOPMENT LABORATORIES, INC., San Leandro, CA (US)

( * ) Notice: Subject to any disclaimer, the term of this patent is extended or adjusted under 35 U.S.C. 154(b) by 0 days.

(21) Appl. No.: 17/320,815

(22) Filed: May 14, 2021

(65) Prior Publication Data

US 2021/0373240 A1   Dec. 2, 2021

Related U.S. Application Data

(60) Provisional application No. 63/030,689, filed on May 27, 2020.

(51) Int. Cl.
*G02B 6/26* (2006.01)
*A61B 90/30* (2016.01)
*G02B 6/255* (2006.01)

(52) U.S. Cl.
CPC ............. *G02B 6/262* (2013.01); *A61B 90/30* (2016.02); *G02B 6/2552* (2013.01); *A61B 2090/306* (2016.02)

(58) Field of Classification Search
None
See application file for complete search history.

(56) References Cited

U.S. PATENT DOCUMENTS

| | | | |
|---|---|---|---|
| 5,729,643 A | 3/1998 | Hmelar et al. | |
| 6,445,851 B1 | 9/2002 | Rakuljic et al. | |
| 6,558,958 B1 | 5/2003 | Pilevar et al. | |
| 8,433,168 B2 | 4/2013 | Filippov et al. | |
| 9,348,090 B2 | 5/2016 | Sasaoka et al. | |
| 9,383,514 B2 | 7/2016 | Iida et al. | |
| 2003/0165291 A1* | 9/2003 | Bhagavatula | G02B 6/262 385/33 |
| 2003/0165292 A1* | 9/2003 | Bhagavatula | G02B 6/4203 385/33 |

(Continued)

FOREIGN PATENT DOCUMENTS

| | | | |
|---|---|---|---|
| CN | 103983435 | * | 8/2014 |
| CN | 103983435 A | | 8/2014 |

OTHER PUBLICATIONS

International Search Report and Written Opinion for Application No. PCT/US2021/032510 dated Oct. 1, 2021 (16 pages).

*Primary Examiner* — Jerry Rahll
(74) *Attorney, Agent, or Firm* — Michael Best & Friedrich LLP (57) ABSTRACT

Fiber optic tapered coupler and methods of manufacturing same. One method of manufacturing a fiber optic tapered coupler arrangement includes providing an output fiber having a first end and a second end opposite the first end. The method also includes applying heat to the first end of the output fiber, wherein the first end expands forming a taper at the first end of the output fiber. The method also includes splicing the tapered first end of the output fiber to a first end of an input fiber, wherein a non-tapered portion of the output fiber has a first diameter and the input fiber has a second diameter different from the first diameter.

20 Claims, 12 Drawing Sheets

(56) References Cited

U.S. PATENT DOCUMENTS

| | | |
|---|---|---|
| 2004/0179797 A1 | 9/2004 | Po et al. |
| 2006/0184162 A1 | 8/2006 | Smith |
| 2015/0177732 A1 | 6/2015 | Rochette et al. |
| 2016/0033721 A1 | 2/2016 | Chen |
| 2017/0240455 A1 | 8/2017 | Chang et al. |
| 2018/0224607 A1 | 8/2018 | Bookbinder et al. |
| 2021/0072462 A1* | 3/2021 | Gui .................. G02B 6/14 |

* cited by examiner

Sample 2 Input Face

FIG. 8A

Sample 13 Input Face

Tapered Fiber Sample 26

FIG. 11A

Tapered Fiber Sample 16

FIBER OPTIC TAPERED COUPLER

RELATED APPLICATIONS

This application claims priority to U.S. Provisional Patent Application No. 63/030,689, filed on May 27, 2020, the entire contents of which are incorporated herein by reference.

FIELD

Embodiments relate to a fiber optic tapered coupler and a method of manufacturing same.

SUMMARY

An optical fiber is a flexible, transparent fiber used for, among other things, transmitting light (or a light signal). Optical fibers are often used in the medical field to provide light or illumination to a surgical site. For example, an optical fiber may be used with an endoilluminator. An endoilluminator is a surgical tool that provides illumination for a surgical operation from inside the body. As another example, an optical fiber may be used with a vitrectomy probe as a means to provide light to a surgical site within a patient's eye. When performing surgery within the small and delicate area of an eye, small gauge optical fibers are desirable to surgeons for use with small gauge cannula insertion system ("CIS") and vitrectomy probes (for example, optical fibers with diameters as small as 250 microns such that the optical fiber may fit inside a 27 gauge needle). However, conventional optical fibers do not provide sufficient light output at such small gauges. A conventional optical fiber refers to an optical fiber that is a single piece of optical fiber with a constant diameter along the entire length of the optical fiber. Therefore, there is a need to develop new technologies for providing a higher light output (as compared to conventional optical fibers) through small optical fibers.

One approach is to splice a larger gauge optical fiber to a smaller gauge optical fiber with a tapered portion between the optical fibers. Splicing generally refers to a technique of joining two distinct pieces of optical fibers end to end, such that the light output from the first optical fiber is the light input to the second optical fiber. A tapered fiber generally refers to a piece of optical fiber that has been modified such that the optical fiber has a first diameter at a first end and a second diameter at a second end, where the first diameter is different from the second diameter. For example, a tapered fiber may have a gradual change in diameter at some location along its length. However, forming a taper on small gauge output fibers, for example, the optical fibers used to perform surgery within the small and delicate area of an eye, is very difficult given how small and flimsy such fibers are. Additionally, optical fibers having a plastic core are preferred in surgical applications due to low costs (as opposed to optical fibers having a glass core, which are more expensive). However, splicing two distinct plastic optical fibers is difficult to achieve due to their low melting points and low elastic modulus.

One attempted solution involves using a machined conical tapered section on the larger gauge input fiber. However, this attempted solution results in removal of the cladding of the fiber. The surface of the machined conical tapered section is very rough. Light is lost through the rough surface resulting in a poor light output. Another attempted solution involves forming a taper on the smaller gauge output fiber using compression. For example, a heating tool may be used to compress an end of the smaller gauge output fiber, forming a taper. However, forming a taper through compression is difficult to develop and perform. Yet another attempted solution involves heating and stretching a larger gauge input fiber to form a single tapered fiber. However, given the stress and weakness of the fiber, it is difficult to achieve a sufficient reduction in diameter, a sufficient fiber length, or a combination thereof. Additionally, this solution requires a long piece of high numerical aperture fiber (for example, approximately eight feet), which is costly.

To solve these and other problems, the embodiments described herein provide, among other things, a fiber optic tapered coupler and method of manufacturing same. Embodiments described herein utilize residual stress left in an optical fiber (due to the extrusion process) in a controlled manner to achieve the tapered portion. According to the embodiments described herein, localized heat expansion is used to create a taper (for example, a tapered portion) on a smaller gauge output fiber. For example, the tapered portion may have a diameter of approximately 375 microns at a larger first end and a diameter of approximately 250 microns at a smaller second end. After forming the tapered portion on the smaller gauge output fiber, the tapered portion is spliced with a larger gauge input fiber. The embodiments described herein provide a tapered portion having a focusing effect that is absent in a traditional end-to-end splice of a larger gauge input fiber to a smaller gauge output fiber. Additionally, embodiments described herein may be implemented with a relatively small piece of high numerical aperture fiber, for example, approximately two inches, and a long piece of regular, inexpensive low numerical aperture fiber, for example, approximately eight feet (as opposed to the attempted solution noted above requiring approximately eight feet of high numerical aperture fiber).

One embodiment provides a method of manufacturing a fiber optic tapered coupler arrangement. The method includes providing an output fiber having a first end and a second end opposite the first end. The method also includes applying heat to the first end of the output fiber, where the first end expands forming a taper at the first end of the output fiber. The method also includes splicing the tapered first end of the output fiber to a first end of an input fiber, where a non-tapered portion of the output fiber has a first diameter and the input fiber has a second diameter different from the first diameter.

Another embodiment provides a fiber optic tapered coupler apparatus. The apparatus includes an optical fiber assembly transmitting light from a light source to a surgical site. The optical fiber assembly includes an input fiber having a first end and a second end opposite the first end. The input fiber has a first diameter. The optical fiber assembly also includes an output fiber having a third end and a fourth end opposite the third end. The output fiber has a tapered portion distal to the third end and coupled to the second end of the input fiber, where a non-tapered portion of the output fiber has a second diameter smaller than the first diameter.

Other aspects and embodiments will become apparent by consideration of the detailed description and accompanying drawings.

DETAILED DESCRIPTION

Before any embodiments are explained in detail, it is to be understood the embodiments are not limited in their application to the details of construction and the arrangement of components set forth in the following description or illustrated in the following drawings. Other embodiments are possible and embodiments described and/or illustrated here are capable of being practiced or of being carried out in various ways.

Figure 1:
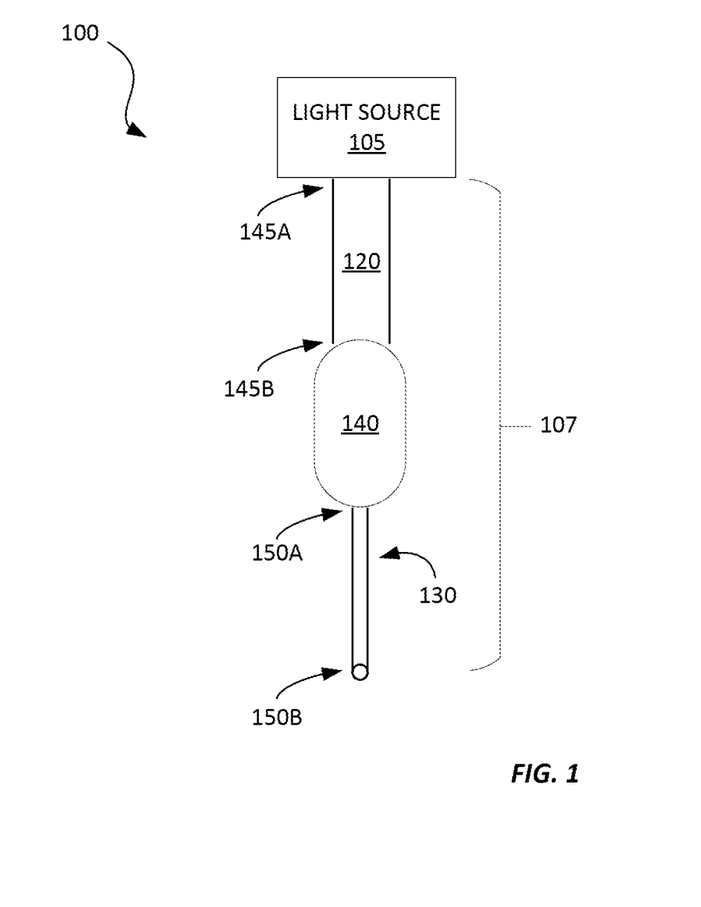
FIG. 1 schematically illustrates a system for providing illumination for a surgical site according to some embodiments.

FIG. 1 schematically illustrates a system 100 for providing illumination for a surgical site according to some embodiments. In the example of FIG. 1, the system 100 includes a light source 105 and an optical fiber assembly 107. In the illustrated example, the optical fiber assembly 107 includes an input fiber 120 coupled to an output fiber 130 by a tapered coupler 140. In some embodiments, the system 100 includes fewer, additional, or different components than those illustrated in FIG. 1.

Figure 7:
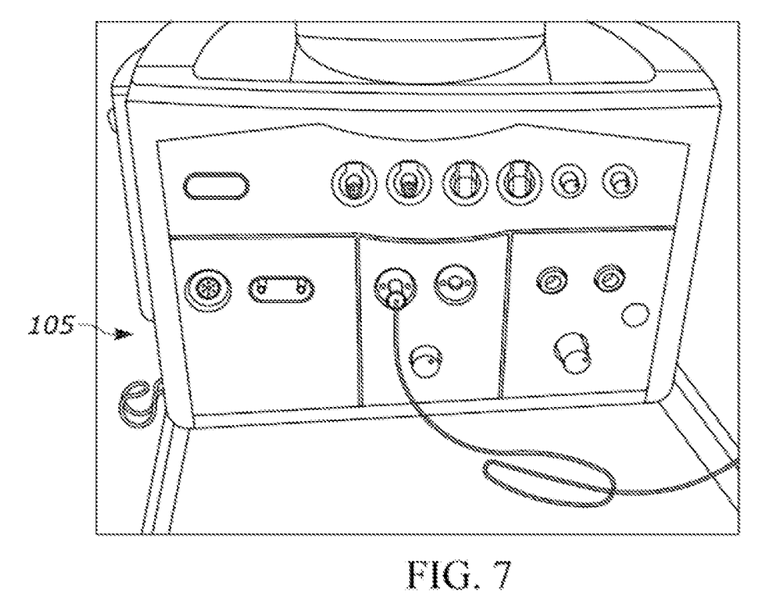
FIG. 7 is a picture of an example light source.

The light source 105 generates light (or a light signal) for transmission to a surgical site, for example, within an eye, via the optical fiber assembly 107. The light source 105 may be, for example, a high-intensity discharge light source, for example, a Nidek Fortas surgical console having a high-intensity discharge light source (as seen in FIG. 7). In the illustrated example, the light source 105 is coupled to the optical fiber assembly 107 (in this case, the input fiber 120).

As seen in FIG. 1, the input fiber 120 includes a first end 145A and a second end 145B and the output fiber 130 includes a first end 150A and a second end 150B. In the illustrated example, the first end 145A is coupled to the light source 105. Accordingly, the first end 145A receives the light generated by the light source 105. The second end 145B is received by (positioned within) the tapered coupler 140 for coupling to the first end 150A of the output fiber 130. The first end 150A of the output fiber 130 is also received by (positioned within) the tapered coupler 140. As noted above, the tapered coupler 140 couples the input fiber 120 to the output fiber 130. Accordingly, the second end 145B of the input fiber 120 and the first end 150A of the output fiber 130 are coupled within (or by) the tapered coupler 140.

The second end 150B outputs the light generated by the light source 105 to a surgical site. Accordingly, in some embodiments, the optical fiber assembly 107 receives the light generated by the light source 105. The received light travels along a length of the optical fiber assembly 107 (for example, the input fiber 120, the tapered coupler 140, and the output fiber 130) to a surgical site to provide illumination within the surgical site. In some embodiments, the second end 150B directly outputs the light to a surgical site. For example, the send end 150B may be inserted into a surgical site and output the light to the surgical site.

Figure 2:
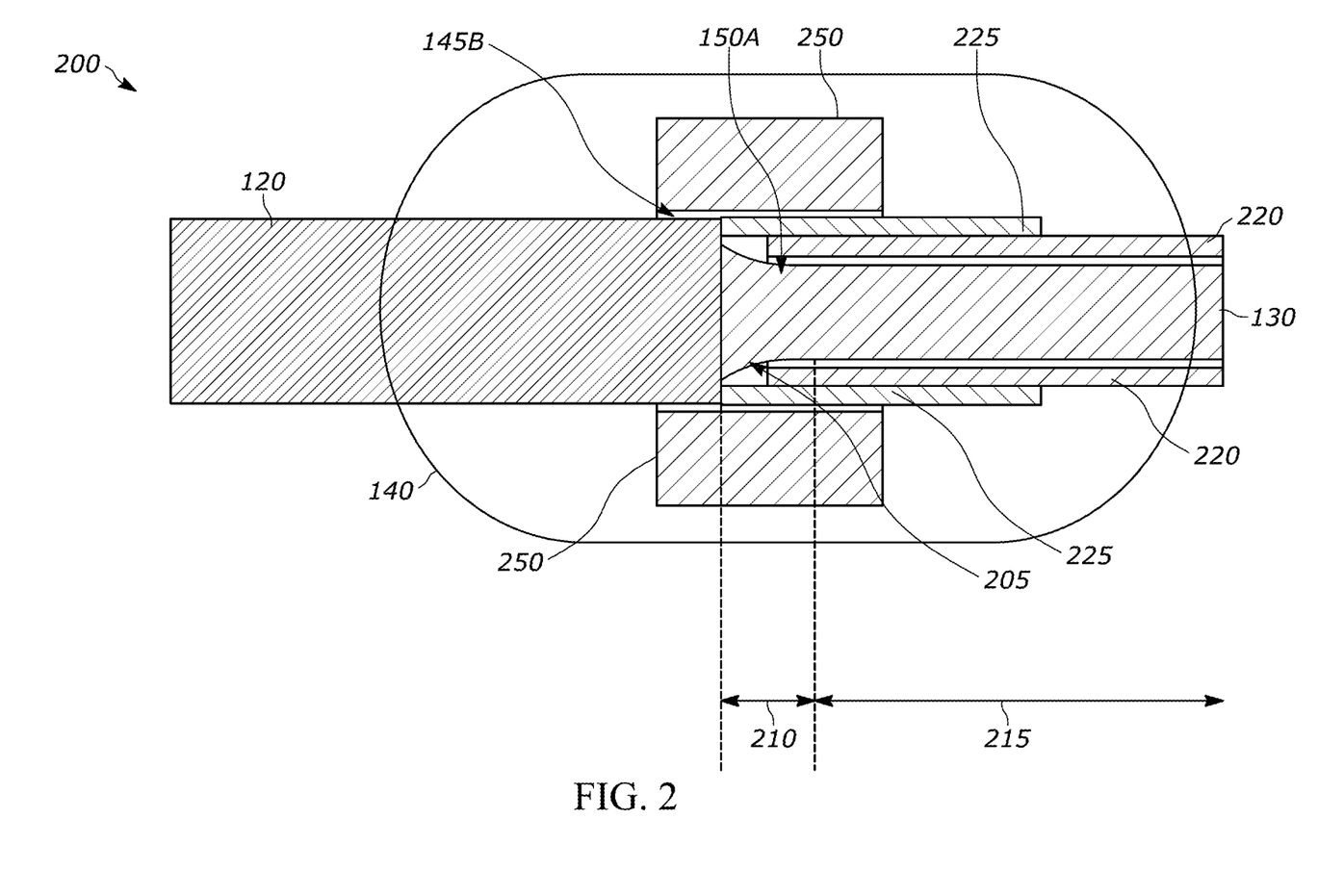
FIG. 2 is a cross-sectional view illustrating a tapered coupler arrangement according to some embodiments.

FIG. 2 is a cross-sectional view of a tapered coupler arrangement 200 according to some embodiments. In the example illustrated, the tapered coupler arrangement 200 includes the tapered coupler 140, the input fiber 120, and the output fiber 130.

As illustrated in FIG. 2, at least a portion of the input fiber 120 (in this case, the second end 145B) is positioned within the tapered coupler 140. In other words, in some embodiments, the tapered coupler 140 receives (or includes) a portion of the input fiber 120. The input fiber 120 may be a single optical fiber (or optical fiber cable). The input fiber 120 has a diameter along its length. In one example, the input fiber 120 has a diameter of approximately 500 microns. In some embodiments, the diameter is a constant (or substantially constant) diameter along the length of the input fiber 120. In other words, a diameter of the input fiber 120 is the same (or substantially the same) between the first end 145A and the second end 145B. In some embodiments, the first end 145A receives the light generated by the light source 105. The received light travels along the length of the input fiber 120 towards the second end 145B.

Additionally, as seen in FIG. 2, at least a portion of the output fiber 130 (in this case, the first end 150A) is positioned within the tapered coupler 140. In some embodiments, the tapered coupler 140 receives (or includes) a portion of the output fiber 130. The output fiber 130 may be a single optical fiber (or optical fiber cable). In the illustrated example, the first end 150A of the output fiber 130 has a taper 205. The taper 205 may be a gradual taper. As described in greater detail below, the taper 205 of the output fiber 130 may be formed through the application of heat to the first end 150A of the output fiber 130.

The output fiber 130 includes a tapered portion 210 and a non-tapered portion 215. The tapered portion 210 includes the taper 205. The tapered portion 210 includes a non-uniform or varying diameter along its length. As seen in FIG. 2, the diameter of the tapered portion 210 changes along its length. For example, when moving from the first end 150A towards the second end 150B, the diameter of the tapered portion 210 decreases. The non-tapered portion 215 has a uniform (or constant) diameter along its length. For example, the non-tapered portion 215 may have a diameter of approximately 250 microns. As seen in the illustrated example, the tapered portion 210 is generally shorter in length than the non-tapered portion 215. In some embodiments, a length of the tapered portion 210 is dependent on a rate of taper for the taper 205 (in this case, how quickly the diameter of the tapered portion 210 changes). For example, a faster or higher rate of taper results in a shorter length of the tapered portion 210. Similarly, a slower or higher rate of taper results in a longer length of the tapered portion 210.

Accordingly, a diameter of the input fiber 120 is different from the diameter of the non-tapered portion 215 of the output fiber 130, where the tapered portion 210 provides a pathway or passage for the light to travel from the input fiber 120 to the output fiber 130. For example, the diameter of the output fiber 130 is smaller than the output fiber 130 (in this case, the non-tapered portion 215 of the output fiber 130). Light is transmitted through a larger gauge input fiber (for example, the input fiber 120) to a smaller gauge output fiber (for example, the output fiber 130) via the tapered portion 210 so that illumination may be provided to a surgical site (for example, within an eye).

In some embodiments, the output fiber 130 (or a portion thereof) is enclosed or encapsulated by one or more additional tubes forming an output fiber assembly. For example, as illustrated in FIG. 2, the output fiber 130 (or a portion thereof) may be enclosed by an output tube 220, a sizing tube 225, another tube, or a combination thereof. The output fiber assembly may include the output fiber 130 (or a portion thereof), the output tube 220, the sizing tube 225, another tube, or a combination thereof. The output tube 220 may include, for example, a tube, a sleeve, or the like. The output tube 220 may surround the output fiber 130 such that the light may travel through the output tube 220 to the surgical site (directly or indirectly via an intermediary surgical device or probe). As one example, the output tube 220 may have an inner diameter configured to accept a diameter of the output fiber 130, for example, a diameter of 250 microns, and an outer diameter configured to be inserted through a 27 gauge cannula. The sizing tube 225 may include, for example, a tube, a sleeve, or the like. As one example, the sizing tube 225 may have an inner diameter configured to accept the output tube 220 and a diameter associated with a maximum diameter of the taper 205, for example, a diameter of 375 microns, and an outer diameter configured to be inserted into an alignment tube.

Additionally, as seen in FIG. 2, the tapered coupler arrangement 200 may include an alignment tube 250. The alignment tube 250 may include, for example, a tube, a sleeve, or the like having an inner diameter configured to accept a diameter of the input fiber 120, for example, a diameter of 500 microns. As one example, the alignment tube 250 may be a support sleeve having a 19 gauge outer diameter and a 25 gauge inner diameter. The alignment tube 250 may provide support and alignment between the input fiber 120 and the output fiber 130. Accordingly, as seen in FIG. 2, the alignment tube 250 may enclose or encapsulate at least a portion of the input fiber 120 and at least a portion of the output fiber assembly (for example, the output fiber 130 (or a portion thereof), the output tube 220, the sizing tube 225, or a combination thereof).

Figure 3:
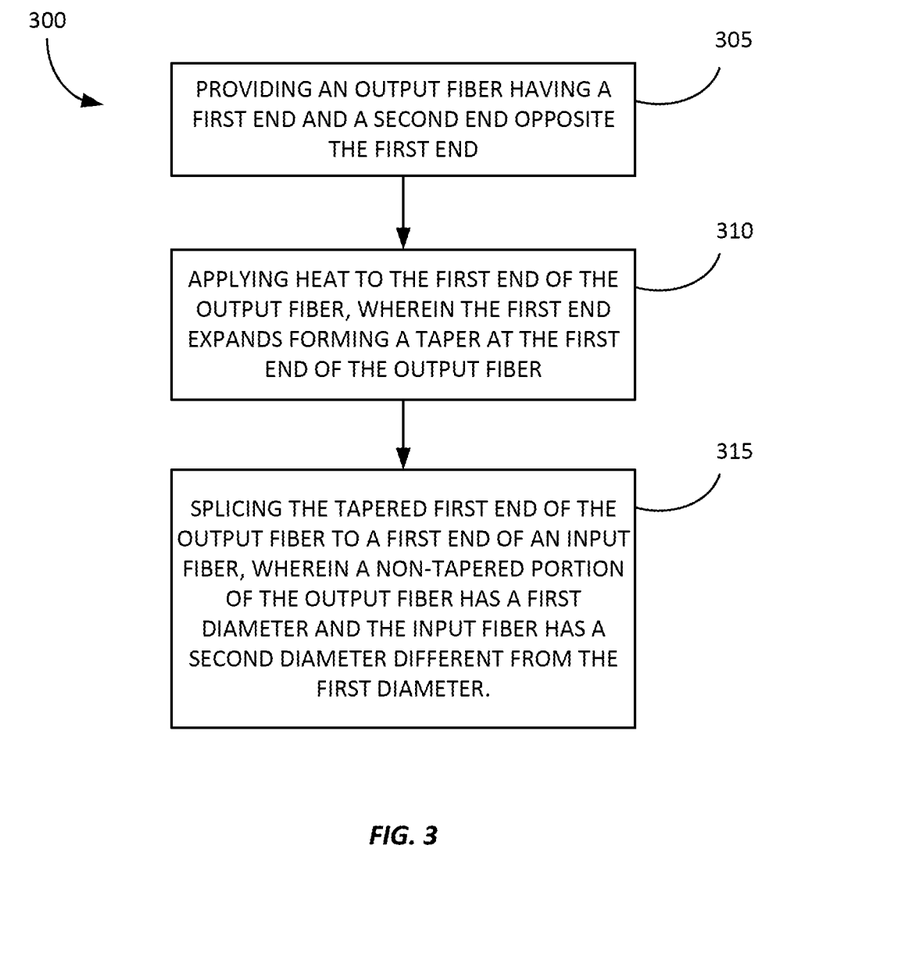
FIG. 3 is a flowchart illustrating a method of manufacturing the tapered coupler arrangement of FIG. 2 according to some embodiments.

FIG. 3 is a flowchart illustrating a method 300 of manufacturing the tapered coupler arrangement 200 of FIG. 2 according to some embodiments. As seen in FIG. 3, the method 300 includes providing the output fiber 130 having the first end 150A and the second end 150B opposite the first end 150A (at block 305). The method 300 also includes applying heat to the first end 150A of the output fiber 130 (at block 310). In some embodiments, localized heat is applied to the first end 150A using, for example, a heating arrangement. The heating arrangement may include, for example, a heat source (for example, a hotplate or a heat gun), a furnace (for example, a custom aluminum part or the like), or a combination thereof. The furnace exposes a portion of the output fiber 130 (for example, the first end 150A) to a temperature gradient such that a smooth and gradual taper is formed. The furnace may result in a temperature decrease along a length of the output fiber 130 (from the first end 150A towards the second end 150B). Additionally, the furnace may result in an expansion decrease along a length of the output fiber 130 (from the first end 150A towards the second end 150B). For example, the first end 150A experiences the highest temperature and the greatest expansion in comparison to an adjacent point along the length of the output fiber 130. The heat source may be set to a temperature between 175° C.-190° C. The first end 150A of the output fiber 130 may be positioned (or inserted) within the furnace. In some embodiments, when the first end 150A is positioned within the furnace, the first end 150A (or a surface thereof) comes into contact with the heat source. The first end 150A of the output fiber 130 may be heated for a period of time, for example, one minute.

Figure 4:
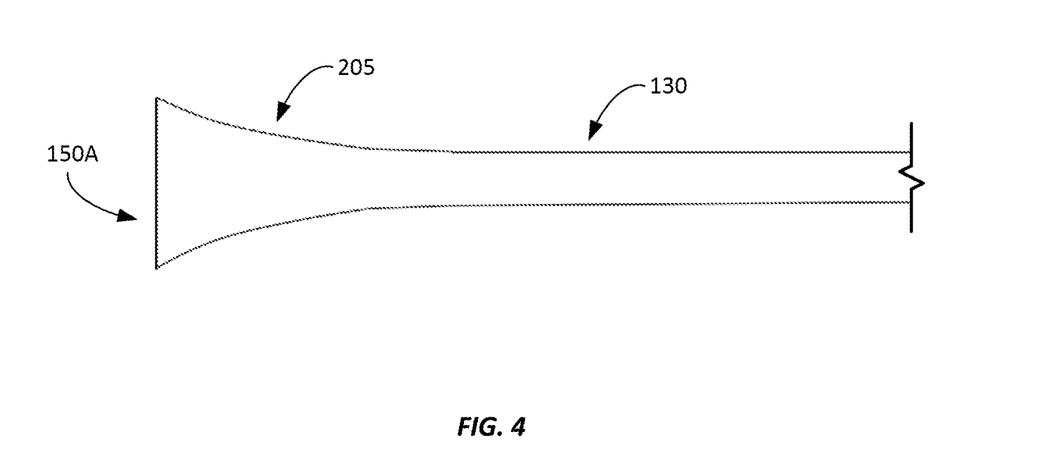
FIG. 4 is a picture of an example tapered optical fiber.

In response to the application of heat, the output fiber 130 (in this case, the first end 150A) experiences expansion. The output fiber 130 experiences expansion as a result of residual stress from the extrusion process used to manufacture optical fibers. The residual stress from extrusion is used to achieve the taper 205 (in this case, the tapered portion 210). FIG. 4 illustrates an example tapered optical fiber. As seen in FIG. 4, the output fiber 130 includes a taper 205, where the taper 205 was formed by the application of heat to the first end 150A of the output fiber 130.

Application of heat softens the material of the output fiber 130, causing the output fiber 130 to deform under the residual stress. Applying heat locally on the first end 150A of the output fiber 130 results in the deformation of the first end 150A under the residual stress. However, the part of the output fiber 130 that is not heated does not expand (for example, the non-tapered portion 215). In some embodiments, the material of the output fiber 130 experiences uniform expansion in multiple directions (for example, in all directions). Therefore, the expansion is uniform expansion in this example.

When light passes through the tapered portion 210, a beam diameter of the light is reduced (to a smaller diameter) as a result of the smaller diameter of the output fiber 130. Additionally, a numerical aperture of the light beam increases. The numerical aperture is related to the maximum angle of light that an optical fiber accepts with respect to its axis. The numerical aperture of a typical plastic optical fiber is 0.5. Since the tapered portion 210 increases this numerical aperture, a high numerical aperture optical fiber may be used as the output fiber 130. For example, the output fiber 130 may have a numerical aperture of approximately 0.7. Accordingly, more light may be accepted by the output fiber 130 as compared to a typical plastic optical fiber having a lower numerical aperture of, for example, 0.5. The more light accepted by the output fiber 130 ultimately results in more illumination or light provided to the surgical site.

In some embodiments, before heat is applied to the first end 150A of the output fiber 130, the output fiber 130 (or a portion thereof) is inserted into a straightening tube. The straightening tube may include, for example, a 20 gauge sleeve. The straightening tube helps keep the output fiber 130 straight during the heating process. Alternatively or in addition, the straightening tube may distribute heat along a length of the output fiber 130, which aids in achieving a smooth and gradual change in diameter (taper). The straightening tube helps prevent or mitigate the output fiber 130 (in this case, the first end 150A) from curling up during the heating process. Accordingly, in such embodiments, the first end 150A of the output fiber 130 and the straightening tube are both positioned within the furnace. After heat is applied to the first end 150A of the output fiber 130 and the straightening tube, the output fiber 130 is removed from the straightening tube.

After the taper 205 is formed on the first end 150A of the output fiber 130, the first end 150A (i.e., a tapered first end 150A) of the output fiber 130 is spliced to the second end 145B of the input fiber 120 (at block 315). As noted above, the non-tapered portion 225 of the output fiber 130 has a different diameter than the diameter of the input fiber 120. Accordingly, the output fiber 130 and the input fiber 120 are coupled via the tapered portion 225 (in this case, the taper 205) so that light may be transmitted from the light source 105 to a surgical site via the optical fiber assembly (in this case, the coupled input fiber 120 and output fiber 130). In some embodiments, the splicing interface is filled with index matching gel, which reduces losses in light energy as the light travels from the input fiber 120 to the output fiber 130.

Sample Building Procedure.

The following describes a sample implementation of the method 300. The inventors implemented the method 300 on thirty sample output fibers. The thirty sample output fibers were high numerical aperture optical fibers having a diameter of 250 microns and a length of approximately four inches ("the Samples").

Figure 5:
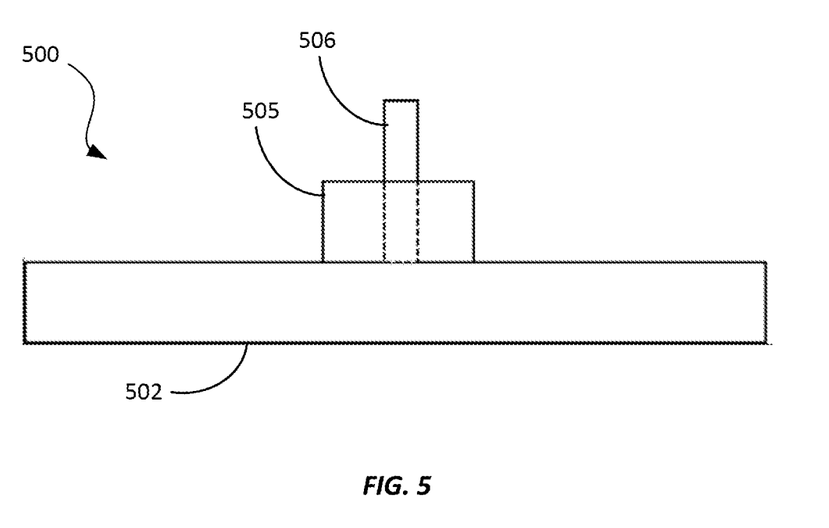
FIG. 5 illustrates a heating arrangement according to some embodiments.

Each Sample was individually exposed to localized heat. For example, FIG. 5 illustrates a heating arrangement 500 used to provide localized heat to the Samples. As seen in FIG. 5, the heating arrangement 500 includes a hotplate 502 and a furnace 505. The hotplate 502 was used as the heat source. The hotplate 502 was set to a temperature of 190° C. for Samples 1-4 while the hotplate 502 was set to a temperature of 175° C. for Samples 5-30. Each Sample was inserted into a 20 gauge output tube (as the straightening tube (represented in FIG. 5 by reference numeral 506) and inserted into the furnace 505 for approximately one minute such that a first end of the Sample (for example, the first end 150A) and an end of the straightening tube 506 both contact the hotplate 502. As described above, the straightening tube 506 helps keep the Sample straight as the taper 205 is formed. In other words, as the first end of the Sample deforms, the straightening tube 506 prevents or mitigates the first end of the Sample from curling up. After one minute, the Sample and the straightening tube 506 were removed from the furnace 505 and allowed to cool for approximately ten seconds. The Sample was then removed from the straightening tube 506. As a result of heating the first end of the Sample, the first end of the Sample becomes tapered, as illustrated in FIG. 4.

A 27 gauge output tube (for example, the output tube 220) was then slipped over the Sample from the smaller end (for example, the second end 150B) and pushed as far as possible towards the taper 205. The output tube 200 was then bonded in place using an adhesive, for example, a cyanoacrylate adhesive (for example, Loctite 4014). The output tube 220 was bonded on the smaller diameter side (in this case, the second end 150B). Next, a 25 gauge sizing tube (for example, the sizing tube 225) was slipped over the bonded output tube 220 from the smaller end (in this case, the second end 150B) and pushed as far as possible towards the taper 205. The sizing tube 225 was bonded in place using the adhesive. The adhesive was applied at the tapered end (in this case, the first end 150A).

Figure 6A:
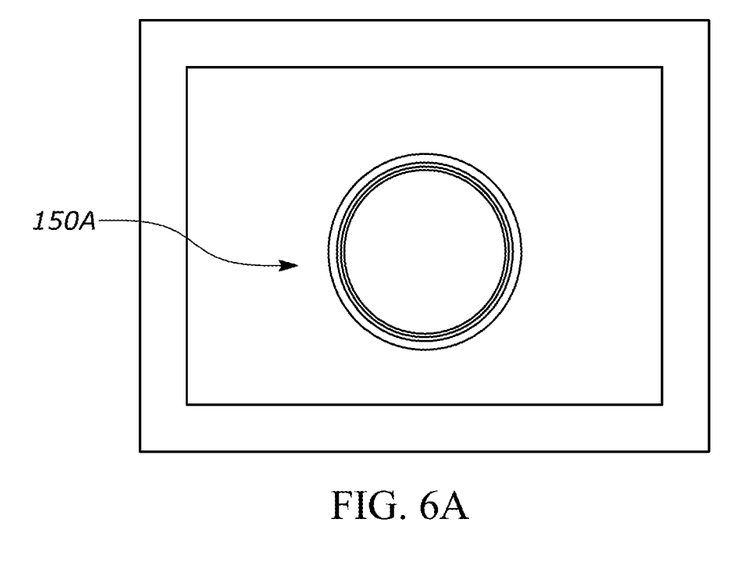
FIGS. 6A-6B are pictures of an input surface and an output surface, respectively, of a tapered fiber.
Figure 6B:
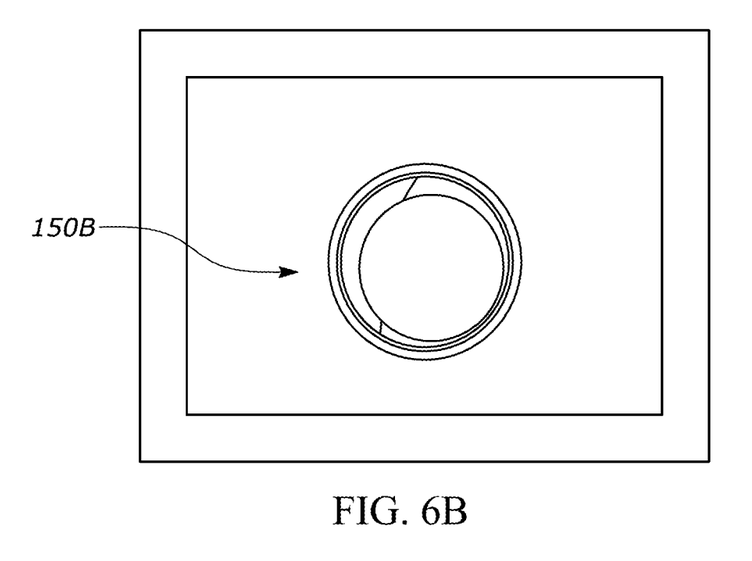

Excess fiber protruding out of the first end, the second end, or a combination thereof was removed using a sharp razor blade. After removing any excess fiber, the ends were polished using polishing films having a grit size of 30 microns, 3 microns, 1 micron, and 0.3 micron, respectively. FIG. 6A is a picture of an input surface of a tapered Sample (for example, the first end 150A) and FIG. 6B is a picture of an output surface of the tapered Sample (for example, a second end 150B). Each end was polished separately and the polishing films were replaced after every three tapered Samples were polished.

A single input fiber (for example, the input fiber 120) was used to deliver light to the tapered Samples. The input fiber 120 was built by polishing the ends of a 500 micron fiber and connected to the light source 105 (via a light source connector). The splicing of the input fiber 120 to the tapered Sample was achieved using a 250 micron support tube (for example, the alignment tube 250). Index matching gel was applied at the interface of the two fibers and the alignment tube 250 was used to maintain alignment. This assembly was not bonded so as to be able to use the input fiber 120 for each of the tapered Samples.

Sample Testing Procedure.

The light source connector on the input end (in this case, the first end 145A) of the input fiber 120 was connected to a light source 105, as shown in FIG. 7. An intensity of the light source 105 was set to 70%. The light source 105 was allowed to stabilize for approximately five minutes before taking light output measurements. Index matching gel was applied to the second end 145B of the input fiber 130. The second end 145B was then mechanically spliced with the tapered first end of a Sample using the alignment tube 250 to maintain alignment. Light output of this testing assembly was measured using a HLMS handheld photometer from Labsphere.

It was found that rotation of the light source connector in the surgical system and rotation of the tapered Sample relative to the input fiber 120 may lead to changes in the light output. It was also found that pressing the two fibers (in this case, the input fiber 120 and the output fiber 130) against each other may increase the light output. Also, the positioning of the second end 150B of the tapered Sample in the opening of the photometer may lead to changes in the light output. The inventors adjusted one or more of these factors to maximize possible light output measurements, which were then recorded. The above steps were repeated to get a second set of independent measurements for each Sample. Sample 24 was scrapped due to damage and Sample 25 was damaged after the first measurement.

Results.

Figure 8A:
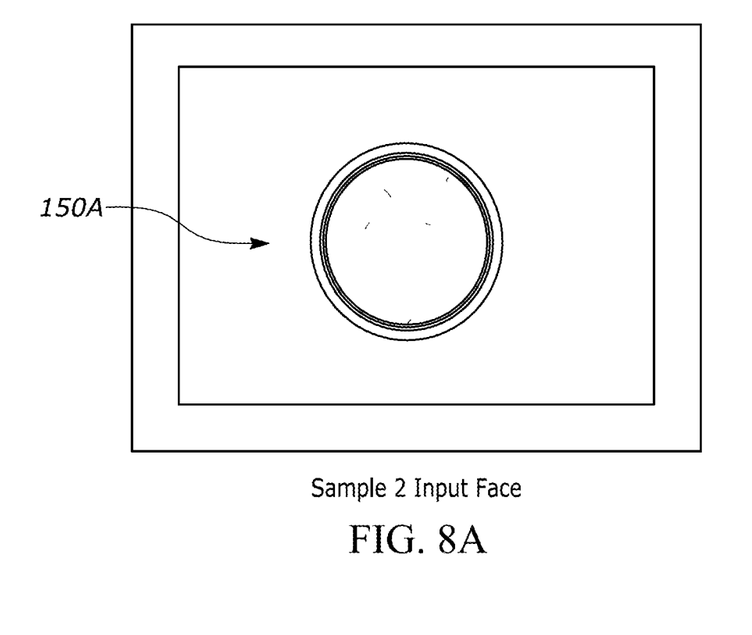
FIGS. 8A-8B are pictures of input surfaces illustrating taper diameters for two tapered fiber samples.
Figure 8B:
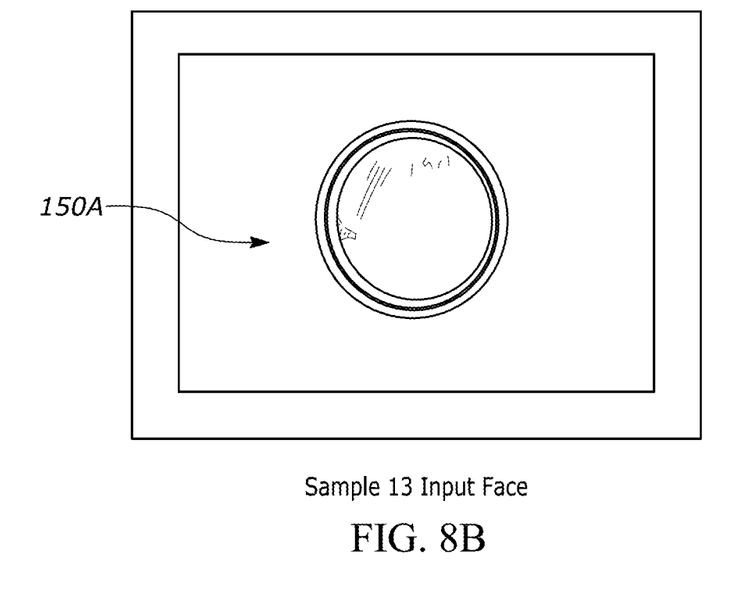

The inventors found that it is possible to achieve a tapered fiber using the methods and systems described herein. The deformation that forms the taper 205 is believed to happen under residual stress in the output fiber 130 left from the extrusion process. As noted above, during the building process, the hotplate temperature was set at 190° C. for the first four Samples and then reduced to 175° C. for the rest of the Samples. As a result, Samples 1-4 experienced a deformation or taper having diameters greater than the inner diameter of the sizing tube 225. These diameters provided a natural stop for the sizing tube 225 and ensured that the inner diameter of the sizing tube 225 is "filled" with the polished face of the output fiber 130 (except for the small space that the adhesive requires). For the rest of the Samples, the maximum diameter of the tapered Sample was not larger than the inner diameter of the sizing tube 225. For these Samples, the "curled up" end of the tapered fiber could act as a stop for the sizing tube 225. Sample 1 and Sample 2, and the maximum light output of all the Samples, may be a contributing factor. An example of this is shown in FIGS. 8A-8B. FIG. 8A is a picture of an input surface (in this case, the first end 150A) of Sample 2 and FIG. 8B is a picture of an input surface (in this case, the first end 150A) of Sample 13. As seen in FIGS. 8A-8B, a slightly larger fraction of the inner diameter of the sizing tube 225 is occupied by Sample 2 as compared to Sample 13.

Figure 9:
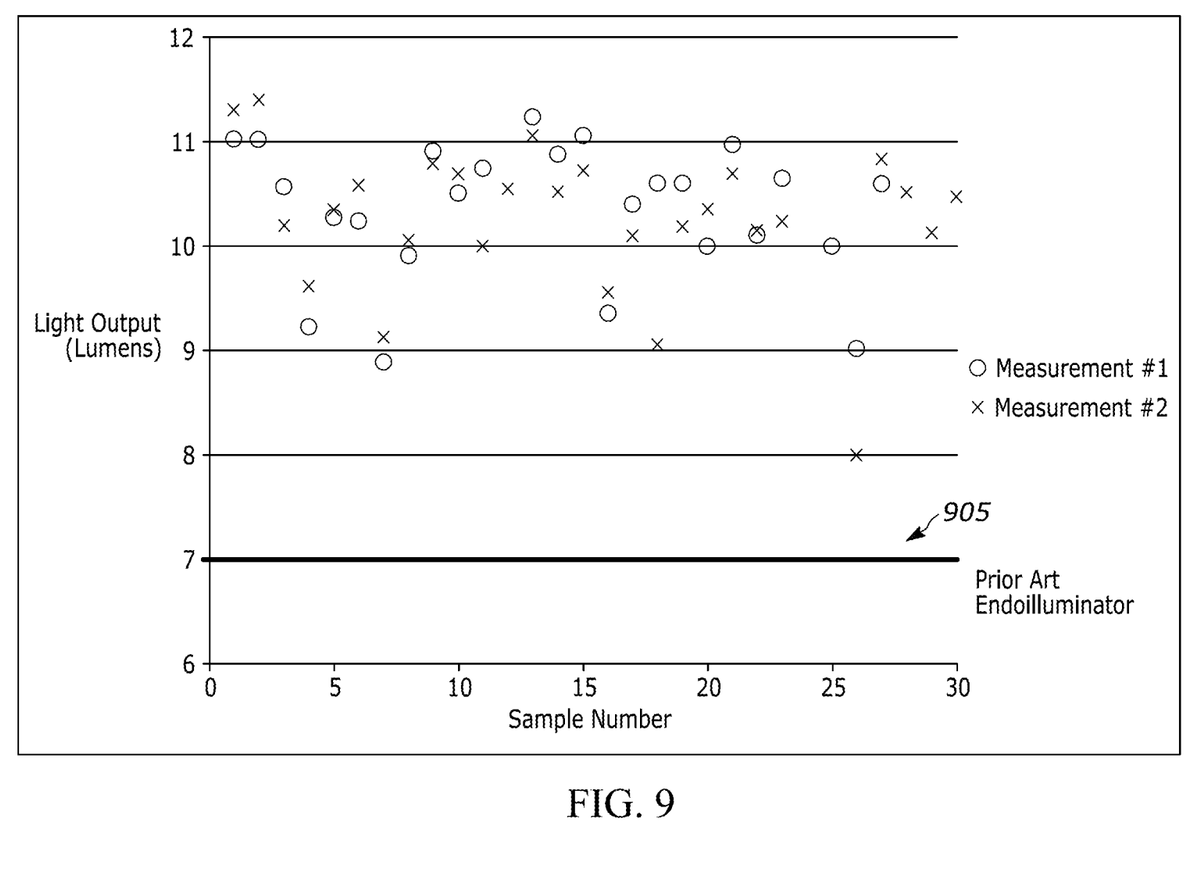
FIG. 9 is a graph illustrating light output measurements of a plurality of tapered fiber samples.

FIG. 9 is a graph illustrating light output measurements. The graph shows the two independent light output measurements made for each of the thirty Samples. A line 905, at the 7 lumen mark, denotes a light output measured from a prior art illumination fiber. A taper-plus-splice approach was used in the prior art fiber. The graph includes the output of only one prior art illumination fiber.

Figure 10:
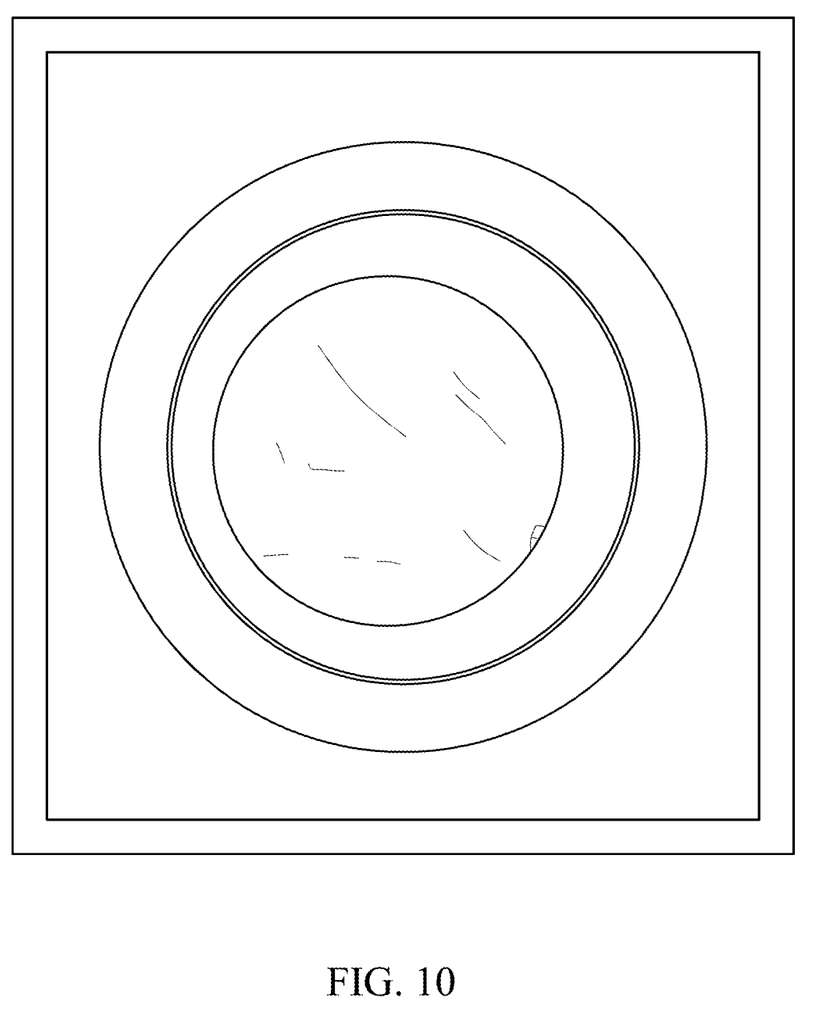
FIG. 10 is a picture of the polished output surface of a tapered fiber sample.

As seen in FIG. 9, all except four of the Samples have a light output greater than 10 lumens. Reasons to explain the lower light output of the four Samples is described below. Some scatter in the light output of the Samples was exhibited. One or more factors are expected to affect the scattering, for example, polish quality, flatness of the polished surface, alignment and placement of the tapered part with the input fiber, cleanliness of the polished surface, and the like. For example, as indicated in the graph of FIG. 9, Sample 7 has one of the lowest light outputs. FIG. 10 is a picture of the polished output surface of Sample 7. Inspection of the polished output surface of Sample 7 showed that the polish quality was not as high as other samples and, as a result, may have contributed to the lower light output shown in the graph of FIG. 9. Despite the scattering exhibited by the Samples, all of the Samples have a higher light output than the prior art illumination fiber.

Figure 11A:
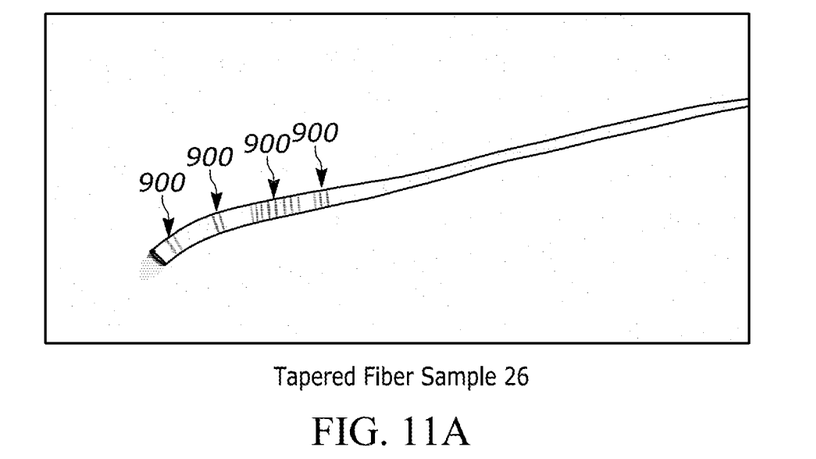
FIGS. 11A-11B are pictures illustrating a plurality of wrinkles formed in two tapered fibers samples.
Figure 11B:
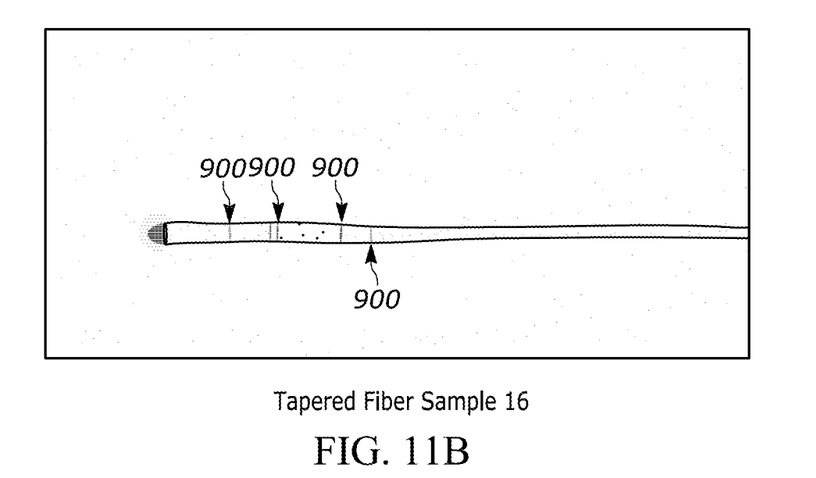
Figure 12A:
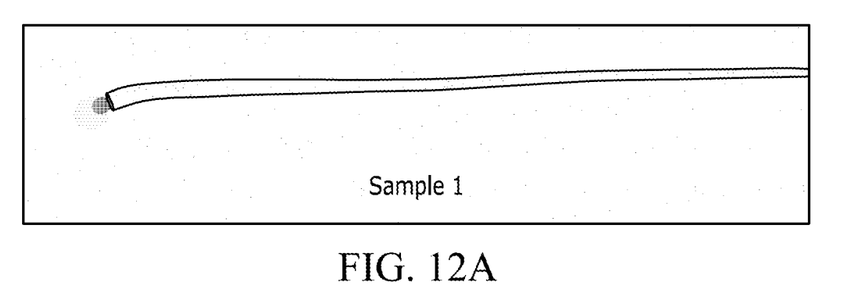
FIGS. 12A-12C are pictures of three tapered fibers samples having the maximum light output.
Figure 12B:
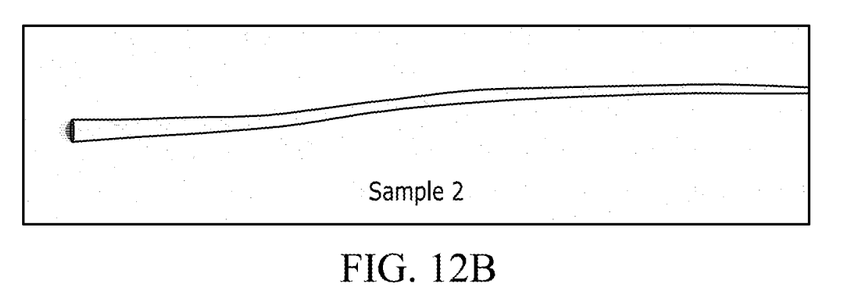
Figure 12C:
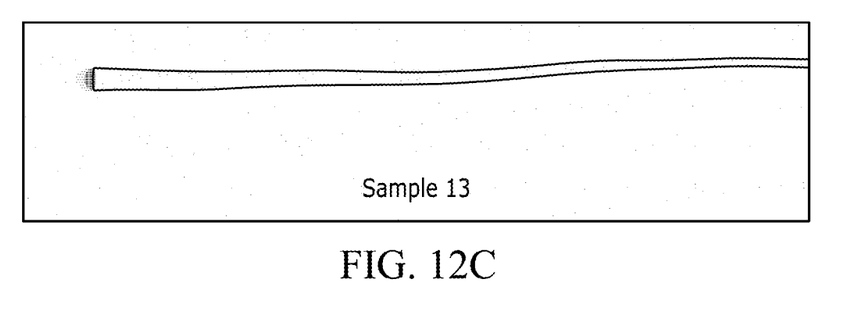

Sample 26 was seen to have a lower light output than the other Samples. One possible reason for this may be defects in the cladding produced as a result of the tapering process. A particular type of defect seen in the tapered Samples is "wrinkling" of the cladding, where light loss is seen through these wrinkles. Most of the tapered Samples include this defect. For example, some Samples include one or two wrinkles while still providing a high light output. However, Sample 26 has an unusually large number of wrinkles. For example, FIG. 11A is a picture of Sample 26. As seen in FIG. 11A, Sample 26 includes a plurality of wrinkles 900. As another example, FIG. 11B is a picture of Sample 16. As seen in FIG. 11B, Sample 16 also includes a plurality of wrinkles. The low light output of Sample 16 and Sample 26 may be explained by the number of wrinkles 900 associated with each respective Sample.

The wrinkles are believed to have been caused due to the non-uniform motion of the core and the cladding of the optical fiber during the heating process. For example, the core deforms after being softened by the heating process. However, the cladding may not have softened as much, which results in the cladding becoming wrinkled. More wrinkling was observed when the motion of the cladding is restricted, for example, by the straightening tube. Accordingly, a straightening tube having approximately an 800 micron diameter was used to keep the optical fiber straight as opposed to, for example, a straightening tube having approximately a 500 micron diameter.

One approach to preventing or mitigating wrinkles involves setting the temperature of the heat source (for example, the hotplate 502) to a higher temperature such that the diameters of the tapered portions 210 (in this case, the tapers 205) are larger than the inner diameter of the sizing tube 225. This may result in wrinkles being in locations where the diameter of the tapered portion 210 is larger than the inner diameter of the sizing tube 225. As noted above, excess fiber protruding out of the first end 150A, the second end 150B, or a combination thereof is removed. Accordingly, when the wrinkles are at a location along the tapered portion 210 where the diameter is larger than the inner diameter of the sizing tube 225, the wrinkles may ultimately be removed as excess fiber protruding out of the first end 150A. For example, FIGS. 11A-11C are pictures of Sample 1, Sample 2, and Sample 13, respectively. As seen from the graph of FIG. 9, Sample 1, Sample 2, and Sample 13 provided the three highest light outputs. As seen in FIGS. 11A-11C, Sample 1, Sample 2, and Sample 13 do not include any wrinkles on each corresponding tapered portion 210.

As another observation, wrinkles on the cladding were rarely observed when the output fiber 130 is heated using a heat gun as the heat source without a straightening tube. This observation may further support that wrinkling on the cladding is caused by some type of restriction on the motion of the cladding, for example, a straightening tube used to keep the output fiber 130 straight.

CONCLUSION

Embodiments described herein relate to developing and manufacturing high output illumination fibers. The methods and systems described herein may be used to manufacture tapered illumination fibers (for example, 27 gauge illumination fibers having a tapered portion). The methods and systems described herein provide illumination fibers that have a larger light output than conventional illumination fibers. The light output provided by the illumination fibers described herein may also be more consistent than conventional illumination fibers. Embodiments described herein utilize localized heating to form a tapered portion on a high numerical aperture fiber, which is then spliced to an output end of a fiber having a larger diameter than the high numerical aperture fiber.

Embodiments described may also help prevent or mitigate wrinkling of the cladding, which may cause loss in light output. Additionally, embodiments described herein may utilize one or more additional factors for maximizing light output, for example, using a higher temperature, firmly pressing spliced surfaces against each other, rotation of a tapered portion, polish quality, careful handling to avoid damage, cleanliness of polished surfaces, and the like.

Thus, the embodiments provide, among other things, a fiber optic tapered coupler and a method of manufacturing same. Various features and advantages of certain embodiments are set forth in the following claims.

What is claimed is:

1. A method of manufacturing a fiber optic tapered coupler arrangement, the method comprising:
   providing an output fiber having a first end and a second end opposite the first end, the output fiber including an outer cladding defining an outer diameter of the output fiber;
   applying heat to the first end of the output fiber, wherein the first end expands such that the outer diameter of the output fiber increases at the first end, forming a taper at the first end of the output fiber; and
   splicing the tapered first end of the output fiber to a first end of an input fiber, wherein a non-tapered portion of the output fiber has a first diameter and the input fiber has a second diameter different from the first diameter.

2. The method of claim 1, wherein the first diameter is smaller than the second diameter.

3. The method of claim 1, further comprising:
   positioning the output fiber within a straightening tube prior to applying heat to the first end of the output fiber, wherein applying heat to the first end includes applying heat to the first end and the straightening tube.

4. The method of claim 3, wherein the straightening tube has a diameter of 500 microns.

5. The method of claim 1, wherein the taper has a non-uniform diameter along a length of the tapered portion.

6. The method of claim 1, further comprising:
after applying heat to the first end of the output fiber, positioning an output tube around a first portion of the output fiber.

7. The method of claim 6, wherein positioning the output tube around the first portion of the output fiber includes sliding the output tube over the second end of the output fiber towards the taper.

8. The method of claim 6, further comprising:
after positioning the output tube, positioning a sizing tube around a second portion of the output fiber larger than the first portion, the sizing tube having a larger diameter than the output tube.

9. The method of claim 6, wherein applying heat to the first end of the output fiber includes applying heat to the first end of the output fiber with a heating apparatus.

10. The method of claim 9, wherein applying heat to the first end of the output fiber with the heating apparatus includes applying heat to the first end of the output fiber with a heat source and a furnace.

11. The method of claim 1, further comprising:
providing, via the output fiber, a light output of 10 lumens.

12. A method of manufacturing a fiber optic tapered coupler arrangement, the method comprising:
providing an output fiber having a first end and a second end opposite the first end;
applying heat to the first end of the output fiber, wherein the first end expands, forming a taper at the first end of the output fiber;
splicing the tapered first end of the output fiber to a first end of an input fiber, wherein a non-tapered portion of the output fiber has a first diameter and the input fiber has a second diameter different from the first diameter;
after applying heat to the first end of the output fiber, positioning an output tube around a first portion of the output fiber; and
after positioning the output tube, positioning a sizing tube around a second portion of the output fiber larger than the first portion, the sizing tube having a larger diameter than the output tube.

13. The method of claim 12, wherein the first diameter is smaller than the second diameter.

14. The method of claim 12, further comprising:
positioning the output fiber within a straightening tube prior to applying heat to the first end of the output fiber, wherein applying heat to the first end includes applying heat to the first end and the straightening tube.

15. The method of claim 14, wherein the straightening tube has a diameter of 500 microns.

16. The method of claim 12, wherein the taper has a non-uniform diameter along a length of the tapered portion.

17. The method of claim 12, wherein positioning the output tube around the first portion of the output fiber includes sliding the output tube over the second end of the output fiber towards the taper.

18. The method of claim 12, wherein applying heat to the first end of the output fiber includes applying heat to the first end of the output fiber with a heating apparatus.

19. The method of claim 18, wherein applying heat to the first end of the output fiber with the heating apparatus includes applying heat to the first end of the output fiber with a heat source and a furnace.

20. The method of claim 12, further comprising:
providing, via the output fiber, a light output of 10 lumens.

* * * * *